United States Patent [19]

Chakrin et al.

[11] 4,015,009
[45] Mar. 29, 1977

[54] PHARMACEUTICAL COMPOSITIONS COMPRISING SUBSTITUTED 3-CINNAMOYL-2H-PYRAN-2,6(3H)-DIONES

[75] Inventors: Lawrence William Chakrin, Haddonfield, N.J.; Kenneth Means Snader, Hatboro, Pa.; Chester Rhodes Willis, Kingston, Jamaica

[73] Assignee: SmithKline Corporation, Philadelphia, Pa.

[22] Filed: Feb. 19, 1976

[21] Appl. No.: 659,305

Related U.S. Application Data

[63] Continuation-in-part of Ser. No. 511,153, Oct. 2, 1974, abandoned.

[30] Foreign Application Priority Data

Sept. 11, 1975 United Kingdom ............ 37418/75

[52] U.S. Cl. ............................. 424/283; 260/240 K
[51] Int. Cl.$^2$ ........................................ A61K 31/35
[58] Field of Search .................................. 424/283

[56] References Cited

UNITED STATES PATENTS

| | | | |
|---|---|---|---|
| 3,849,565 | 11/1974 | Pfister et al. | 424/283 |
| 3,864,493 | 2/1975 | Cairns et al. | 424/283 |
| 3,879,544 | 4/1975 | Reisner et al. | 424/337 |

OTHER PUBLICATIONS

Physicians Desk Reference (PDR), 1974, pp. 760–761.

Primary Examiner—Norman A. Drezin
Attorney, Agent, or Firm—Richard D. Foggio; William H. Edgerton

[57] ABSTRACT

Pharmaceutical compositions comprising a substituted 3-cinnamoyl-2H-pyran-2,6(3H)-dione and methods of inhibiting the antigen-antibody reaction by administering said compositions. Certain of the 3-cinnamoyl-2H-pyran-2,6(3H)-diones are novel compounds per se.

12 Claims, No Drawings

PHARMACEUTICAL COMPOSITIONS COMPRISING SUBSTITUTED 3-CINNAMOYL-2H-PYRAN-2,6(3H)-DIONES

This application is a continuation-in-part of application Ser. No. 511,153 filed Oct. 2, 1974, now abandoned.

This invention relates to novel pharmaceutical compositions which inhibit certain antigen-antibody reactions and to methods of inhibiting such antigen-antibody reactions by administering said compositions. More specifically, the compositions of this invention comprise a substituted 3-cinnamoyl-2H-pyran-2,6(3H)-dione as the active medicament.

The novel pharmaceutical compositions of this invention comprise a nontoxic pharmaceutical carrier or diluent and a substituted 3-cinnamoyl-2H-pyran-2,6(3H)-dione of the following general structural formula:

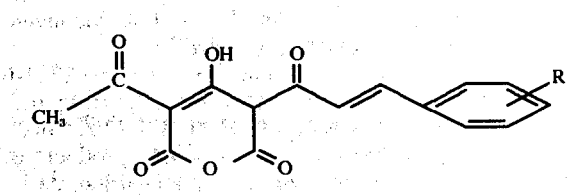

wherein R represents hydrogen, methoxy, dimethoxy, hydroxy, methyl, carboxymethyleneoxy, acetamido or 3-acetamido-4-hydroxy.

Advantageously the compositions of this invention comprise a compound of formula I above when R is hydroxy, carboxymethyleneoxy or acetamido.

The compounds of formula I are generally prepared as shown in the following reaction scheme:

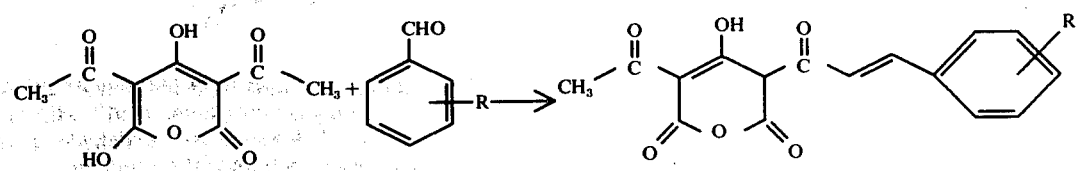

in which R is as defined above. Thus, 3,5-diacetyl-4,6-dihydroxy-2H-pyran-2-one and the benzaldehyde are usually heated at reflux in an inert organic solvent such as chloroform and in the presence of piperidine for from 4 to 36 hours. The pyran starting material is obtained by reaction of acetonedicarboxylic acid and acetic anhydride in sulfuric acid at elevated temperature.

Certain of the compounds of formula I above are novel compounds and as such form a part of this invention. These compounds may be represented by the following formula:

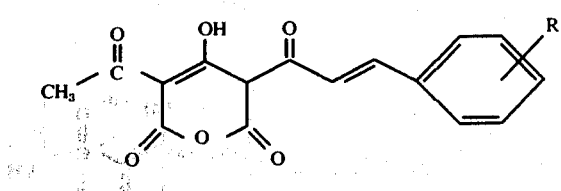

wherein R represents hydroxy, carboxymethyleneoxy, acetamido or 3-acetamido-4-hydroxy.

The compositions of this invention inhibit the release and/or formation of pharmacologically active mediators from effector cells triggered by the interaction of antigen and a specific antibody fixed to the cell surface. Thus the compositions are valuable in the treatment of allergic diseases such as asthma, rhinitis and urticaria.

The inhibitory activity of the compositions of this invention on mediator release in sensitized tissues is measured by the ability of the active medicament to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-Bordatella pertussis U.S.P. i.p.-and N. Brasiliensis i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal, may be employed). Percent inhibition is calculated from the difference in mean average wheal diameter between a treated group and saline or appropriate diluent controls.

The compounds of formula I administered intravenously to rats at doses of from 0.5 to 10 mg/kg produce marked inhibition of the PCA reaction. A preferred compound, 5-acetyl-3-(p-hydroxycinnamoyl)-4-hydroxy-2H-pyran-2,6(3H)-dione, produced 48% inhibition of the rat PCA wheal at 1.5 mg/kg i.v. Another preferred compound, 5-acetyl-3-[p-(carboxymethyleneoxy)cinnamoyl]-4-hydroxy-2H-pyran-2,6-(3H)-dione, produced 50% inhibition of the rat PCA wheal at 0.5 mg/kg, i.v. In testing for mechanism of action, the compounds of formula I were found not to provide comparable inhibition of wheals of approximately equal severity produced in rats by the intracutaneous administration of histamine and serotonin following i.v. administration of the test compound at the same dose and pretreatment time which exhibited significant inhibition of the rat 48 hour PCA reaction.

Upon oral administration, 5-acetyl-3-(m-hydroxycinnamoyl)-4-hydroxy-2H-pyran-2,6(3H)-dione produced 29% inhibition in the rat 48 hour PCA system at 25 mg/kg and a pretreatment time of 15 minutes.

The pharmaceutical compositions of this invention comprise an appropriate amount of a substituted 3-cinnamoyl-2H-pyran-2,6(3H)-dione as set forth in formula I in association with a pharmaceutical carrier or diluent. The nature of the composition and the pharmaceutical carrier or diluent will of course depend upon the intended route of administration, i.e. orally, parenterally or by inhalation. Preferably the active medicament is administered to an animal in a composition comprising an amount sufficient to produce an inhibition of the consequences of the antigen-antibody reaction. When employed in this manner, the dosage of composition is such that from 5 mg. to 500 mg. of active ingredient are administered at each administration. Advantageously equal doses will be administered 1 to 4 times daily with the daily dosage regimen being about 5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g., lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredients.

As a specific embodiment of a useful composition, the active ingredient such as 5-acetyl-3-(p-hydroxycinnamoyl)-4-hydroxy-2H-pyran-2,6(3H)-dione, is dissolved in sterile water at a concentration of 0.5% and aerosolized from a nebulizer operating at an air flow adjusted to deliver the desired aerosolized weight of drug.

A wide variety of other pharmaceutical forms can be employed. Thus, if a solid carrier is used the preparation can be tableted, placed in a hard gelatin capsule in powder or pellet form, or in the form of a troche or lozenge for oral administration. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

The method in accordance with this invention also includes inhibiting the effects of the antigen-antibody reaction which comprises the prior application to the area of the antigen-antibody mechanism a therapeutically effective amount of a substituted 3-cinnamoyl-2H-pyran-2,6(3H)-dione as defined in formula I. A particular application is a method of relieving or preventing allergic airway obstruction which comprises administering to an animal a therapeutically effective amount at suitable intervals.

The pharmaceutical preparations are made following the conventional techniques of the pharmaceutical chemist involving mixing, granulating and compressing when necessary, or variously mixing and dissolving the ingredients as appropriate to the desired end product.

The accompanying examples illustrate the preparation of compounds of formula I and their incorporation into pharmaceutical compositions of this invention and as such are not to be considered as limiting the invention set forth in the claims appended hereto.

Kiang, A. K. et al. J. Chem. Soc. (c) pp. 2721-6 (1971) have questioned the structure assigned by previous authors such as Wiley, R. H. et al. J. Org. Chem. 21:686–688 (1956) to the reaction product of acetonedicarboxylic acid and acetic anhydride, designated 5-carboxydehydroacetic acid. Thus, Kiang et al. supra reported that the reaction of acetondicarboxylic acid with acetic anhydride gave the compound of structure III.

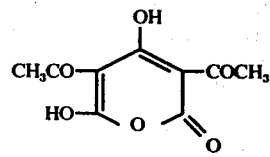

Wiley et al. supra have also reported condensation products of "5-carboxydehydroacetic acid" with p-dimethylamino-and 2,3-dimethoxybenzaldehyde and assigned the following structure to the products:

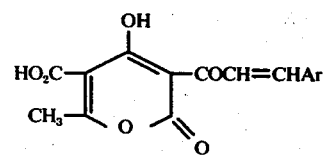

Upon investigation which has included $^{13}C$ nuclear magnetic resonance spectral studies, we have concluded that the reaction of acetondicarboxylic acid with acetic anhydride gives a product having the tautomeric structure as shown below:

A.

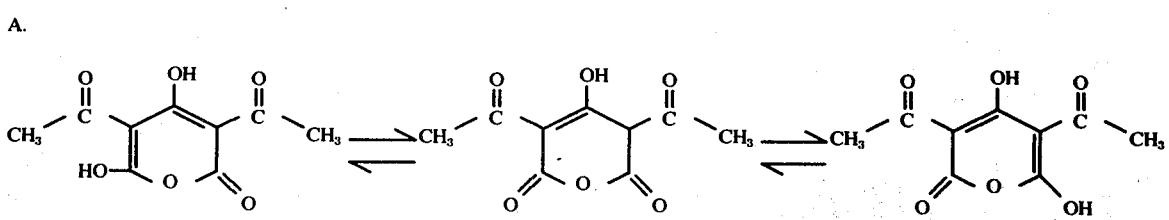

For convenience this product is designated herein as 3,5-diacetyl-4,6-dihydroxy-2H-pyran-2-one. This agrees with Kiang et al's gross structure indicated by formula III above. The rate of tautomerization represented by A above is affected, among other factors, by the solvent used in the $^{13}C$ spectral study. Accordingly, the reaction of this produced with a benzaldehyde, $RC_6H_4CHO$, gives a product having the tautomeric structures as shown below:

B.

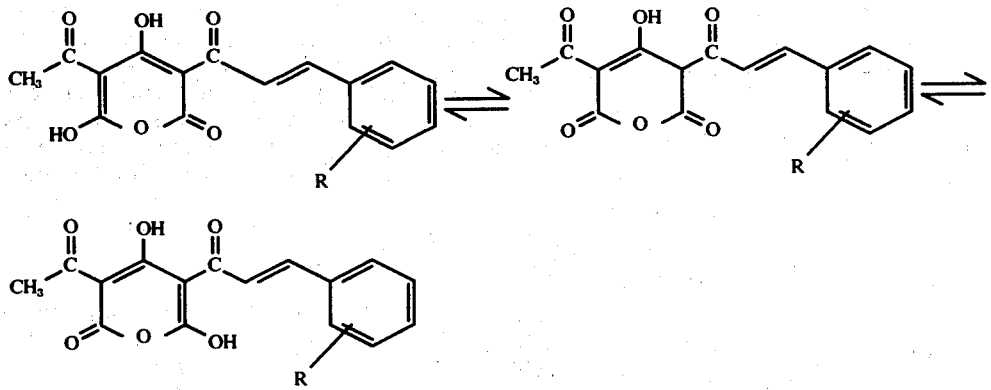

in which R is as defined above for formula I. For convenience, one tautomeric form has been chosen, namely the intermediate pyran-2,6-dione structure, to represent the compounds formed by reaction of A with a benzaldehyde, $RC_6H_4CHO$, as indicated by formula I above.

EXAMPLE 1

A mixture of 8.48 g. (0.04 m.) of 3,5-diacetyl-4,6-dihydroxy-2H-pyran-2-one, 4.88 g. (0.04 m.) of p-hydroxybenzaldehyde in 100 ml. of chloroform and 20 drops of piperidiene is refluxed for 12 hours. The cooled reaction mixture is filtered and the filrate is concentrated to give the starting pyran. The original solid is treated with acetone/water to yield 5-acetyl-3-(p-hydroxycinnamoyl)-4-hydroxy-2H-pyran-2,6(3H)-dione, m.p. 235°–237° C.

Similarly, 8.48 g. of 3,5-diacetyl-4,6-dihydroxy-2H-pyran-2-one, 4.90 g. of m-hydroxybenzaldehyde, 35 drops of piperidine and 200 ml. of cloroform is refluxed for 12 hours and the resulting precipitate is removed by filtration to give 5-acetyl-3-(m-hydroxycinnamoyl)-4-hydroxy-2H-pyran-2,6(3H)-dione, m.p. 194°–196° C.

EXAMPLE 2

Following the procedure of Example 1, a mixture of 8.48 g. (0.04 m.) of 3,5-diacetyl-4,6-dihydroxy-2H-pyran-2-one, 4.8 g. (0.04 m.) of p-methylbenzaldehyde in 100 ml. of chloroform and 20 drops of piperidine is refluxed for 10 hours, concentrated and filtered to yield 5-acetyl-4-hydroxy-3-(p-methylcinnamoyl)-2H-pyran-2,6(3H)-dione, m.p. 188°–190° C.

EXAMPLE 3

A mixture of 4.24 g. of 3,5-diacetyl-4,6-dihydroxy-2H-pyran-2-one, 2.12 g. of benzaldehyde, 20 drops of piperidine and 75 ml. of chloroform is refluxed for eight hours. The water liberated during the reaction is removed by a receiver. The reaction mixture is concentrated and triturated with ethanol to afford 5-acetyl-3-cinnamoyl-4-hydroxy-2H-pyran-2,6(3H)-dione, m.p. 154°–155° C.

EXAMPLE 4

3,5-Diacetyl-4,6-dihydroxy-2H-pyran-2-one (8.48 g., 0.04 m.) 6.65 g. (0.04 m.) of 2,5-dimethoxybenzaldehyde in 50 ml. of chloroform and 20 drops of piperidine are refluxed for 8 hours. The reaction mixture is cooled and filtered to give 5-acetyl-3-(2,5-dimethoxycinnamoyl)-4-hydroxy-2H-pyran-2,6(3H)-dione, m.p. 194°–195° C.

Similarly, equimolar amounts of 3,5-diacetyl-4,6-dihydroxy-2H-pyran-2-one and 3,4-dimethoxybenzaldehyde or 2,3-dimethoxybenzaldehyde are reacted as above to yield the products, 5-acetyl-3-(3,4-dimethoxycinnamoyl)-4-hydroxy-2H-pyran-2,6(3H)-dione, m.p. 223°–225° C., and 5-acetyl-3-(2,3-dimethoxycinnamoyl)-4-hydroxy-2H-pyran-2,6(3H)-dione, m.p. 175°–176° C., respectively.

EXAMPLE 5

Following the procedure of Example 1, equimolar amounts of 3,5-diacetyl-4,6-dihydroxy-2H-pyran-2-one and p-methoxybenzaldehyde or m-methoxybenzaldehyde are reacted to furnish 5-acetyl-4-hydroxy-3-(p-methoxycinnamoyl)-2H-pyran-2,6(3H)-dione, m.p. 182°–184° C., and 5-acetyl-4-hydroxy-3-(m-methoxycinnamoyl)-2H-pyran-2,6(3H)-dione, m.p. 180°–182° C., respectively.

EXAMPLE 6

A mixture of 4.2 g. (0.02 m.) of 3,5-diacetyl-4,6-dihydroxy-2H-pyran-2-one, 3.6 g. (0.02 m.) of 4-formylphenoxyacetic acid, 200 ml. of chloroform and 30 drops of piperidine is azeotroped under reflux for 24 hours. The reaction mixture is filtered to give 5-acetyl-3-[p-(carboxymethyleneoxy)cinnamoyl]-4-hydroxy-2H-pyran-2,6(3H)-dione, m.p. 218.5°–221° C.

EXAMPLE 7

To a mixture of 2.11 g. (0.01 m.) of 3,5-diacetyl-4,6-dihydroxy-2H-pyran-2-one and 1.63 g. (0.01 m.) of p-acetamidobenzaldehyde in 200 ml. of chloroform is added with stirring 25 drops of piperidine. The resulting solution is refluxed and azeotroped for 12 hours, filtered hot and the solid is washed with dilute hydrochloric acid, water and ether to give 3-(p-acetamidocinnamoyl)-5-acetyl-4-hydroxy-2H-pyran-2,6(3H)-dione, m.p. 230°–231° C.

Similarly, 4.2 g. (0.02 m.) of 3,5-diacetyl-4,6-dihydroxy-2H-pyran-2-one, 3.2 g. (0.02 m.) of m-acetamidobenzaldehyde, 200 ml. of chloroform and 0.5 ml. of piperidine is azeotroped for four hours and the reaction mixture is filtered to yield 3-(m-acetamidocinnamoyl)-5-acetyl-4-hydroxy-2H-pyran-2,6(3H)-dione, m.p. 222°-224° C.

EXAMPLE 8

A mixture of 2.96 g. (0.014 m.) of 3,5-diacetyl-4,6-dihydroxy-2H-pyran-2-one, 2.5 g. (0.014 m.) of 3-acetamido-4-hydroxybenzaldehyde (prepared from 3-amino-4-hydroxybenzalaldehyde by reaction with acetic anhydride/sodium acetate), 200 ml. of chloroform and 35 drops of piperidine is refluxed, stirred and azeotroped for 36 hours. Filtration gives a solid which is washed with dilute hydrochloric acid and chloroform. The dried solid is placed in a Soxhlet apparatus and extracted with acetone for several hours. The acetone extract is evaporated and the solid is washed with chloroform, then triturated with ether to furnish 3-[(3-acetamido-4-hydroxy)cinnamoyl]-5-acetyl-4-hydroxy-2H-pyran-2,6(3H)-dione, m.p. 237°-239° C.

EXAMPLE 9

For oral administration, compositions such as the following can be prepared:

| Ingredients | Mg./Capsule |
| --- | --- |
| 5-Acetyl-3-(m-hydroxycinnamoyl)-4-hydroxy-2H-pyran-2,6(3H)-dione | 50 |
| Magnesium stearate | 5 |
| Lactose | 350 |

The above ingredients are screened through a No. 40 mesh screen, mixed and filled into No. 0 hard gelatin capsules.

What is claimed is:

1. A pharmaceutical composition for inhibiting the symptoms of asthma comprising a nontoxic pharmaceutical carrier or diluent and an amount sufficient to produce said inhibition of a compound of the formula:

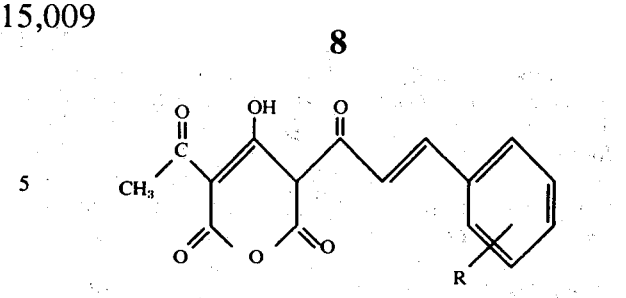

wherein R is hydrogen, methoxy, dimethoxy, hydroxy, methyl, carboxymethyleneoxy, acetamido or 3-acetamido-4-hydroxy.

2. A pharmaceutical composition according to claim 1 in a form suitable for administration by inhalation.

3. A pharmaceutical composition according to claim 1 comprising a solution or suspension of the active ingredient in sterile water.

4. A pharmaceutical composition according to claim 1 in the form of an aerosol formulation.

5. A pharmaceutical composition according to claim 1 in which the pharmaceutical carrier or diluent is a solid.

6. A pharmaceutical composition according to claim 1 in which R is hydroxy, carboxymethyleneoxy or acetamido.

7. A pharmaceutical composition according to claim 6 in which R is hydroxy.

8. A pharmaceutical composition according to claim 7 in which R is p-hydroxy.

9. A pharmaceutical composition according to claim 1 in dosage unit form and in which the active ingredient is in an amount of about 5 mg. to about 500 mg. per dosage unit.

10. The method of inhibiting the symptoms of asthma which comprises administering to an animal in need thereof a therapeutically effective amount for producing said inhibition of a compound of the formula.

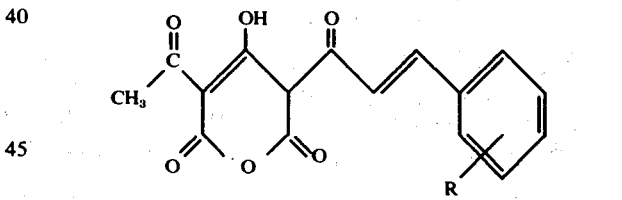

wherein R is hydrogen, methoxy, dimethoxy, hydroxy, methyl, carboxymethyleneoxy, acetamido or 3-acetamido-4-hydroxy.

11. The method of claim 10 in which the active ingredient is administered in a daily dosage regimen of about 5 mg. to about 2000 mg.

12. The method according to claim 10 in which R is p-hydroxy.

* * * * *